United States Patent [19]

Pisharodi

[11] Patent Number: 5,123,926
[45] Date of Patent: Jun. 23, 1992

[54] ARTIFICIAL SPINAL PROSTHESIS

[76] Inventor: Madhavan Pisharodi, 500 Acacia Lake Dr., Brownsville, Tex. 78521

[21] Appl. No.: 659,757

[22] Filed: Feb. 22, 1991

[51] Int. Cl.⁵ .................... A61F 2/44; A61F 2/04
[52] U.S. Cl. .......................... 623/17; 623/12; 623/18; 606/60; 606/61; 606/63
[58] Field of Search .............. 623/17, 18, 12; 606/60, 606/61, 63

[56] References Cited

U.S. PATENT DOCUMENTS

| | | |
|---|---|---|
| 3,648,294 | 3/1972 | Shahrastani . |
| 3,867,728 | 2/1975 | Stubstad et al. . |
| 4,309,777 | 1/1982 | Patil . |
| 4,759,769 | 7/1988 | Hedman et al. . |
| 4,834,757 | 5/1989 | Brantigan . |
| 4,863,476 | 9/1989 | Shepperd . |
| 4,863,477 | 9/1989 | Monson ............................ 623/17 |
| 4,904,260 | 2/1990 | Ray et al. ........................ 623/17 |
| 4,904,264 | 2/1990 | Scheunemann ................. 623/18 |
| 4,919,668 | 4/1990 | Rosenbaum et al. ........... 623/18 |
| 4,932,969 | 6/1990 | Frey ................................. 623/17 |
| 4,932,975 | 6/1990 | Main et al. ...................... 623/17 |
| 5,002,576 | 3/1991 | Fuhrmann et al. ............. 623/17 |

FOREIGN PATENT DOCUMENTS 1124955 11/1984 U.S.S.R. .......................... 606/61

Primary Examiner—Randy C. Shay
Assistant Examiner—D. Willse
Attorney, Agent, or Firm—Vaden, Eickenroht, Thompson, & Boulware

[57] ABSTRACT

An artificial disk prosthesis and methods for implanting it, the prosthesis. In one embodiment having a member for adapting in size and shape to an anatomical space between vertebrae and apparatus for expanding the member to conform to the space.

12 Claims, 1 Drawing Sheet

ARTIFICIAL SPINAL PROSTHESIS

RELATED APPLICATION

Filed on even date herewith is Applicant's application entitled Artificial Middle Expandable Intervertebral Disk Implants, a copy of which is submitted herewith.

BACKGROUND OF THE INVENTION

1. Field of the Invention

This invention relates to an artificial intervertebral prosthesis. More particularly, the present invention relates to a stable, yet flexible, synthetic intervertebral disk prosthesis for insertion into a spine following removal of a natural disk.

2. Description of the Related Art

The spine is a flexible structure comprised of thirty-three vertebrae. The vertebrae are separated and cushioned from each other by fibro-cartilaginous structures called the intervertebral disks. If the spine is injured or becomes diseased, these disks may be surgically removed.

The present treatment of lumbar disk herniation is a compromised functional recovery at best. The disk that has come out of its place has no physiological function and at this time no method is known that will bring back the functional lumbar disk. A disk prosthesis is needed which can be applied to the disk space and provide the cushioning effect for the disk that is expected of the normal disk.

Several unacceptable attempts have been made to solve these problems; such as applying spring loaded disk prosthesis or saline injectable disks with suction cups on the surfaces. The spring loaded disk is so bulky it cannot be inserted into the disk space through the limited opening that is available for this kind of surgery. The saline injectable disk is unstable and the suction cups do not hold it onto the vertebral bodies with their irregular spikey surfaces.

Various methods have been employed to deal with the problems that occur after disk removal. One common procedure has been, after disk removal, to fuse the vertebrae that were previously separated from the disk. Unfortunately, this procedure virtually precludes any degree of spinal flexibility. Similarly, disk removal has been followed by replacement with a disk prosthesis purportedly designed to replicate a natural disk's function. However, although artificial disk prostheses have been developed, none are completely satisfactory.

U.S. Pat. No. 4,309,777 to Patil discloses an artificial disk having a plurality of springs positioned between lower and upper disk portions. In addition, a plurality of spikes extend from the upper and lower portions of the disk to engage the vertebrae. U.S. Pat. No. 4,759,769 to Hedman discloses an artificial spinal disk comprised of upper and lower portions connected by both hinge and spring devices. The Patil and Hedman disks, albeit stable, lack a physiological structure and therefore are not used. U.S. Pat. No. 4,834,757 to Bramtigan discloses vertebral implant plugs on blocks useful in fusing together adjoining vertebral bodies. U.S. Pat. No. 4,863,476 to Sheppard discloses an elongated spinal implant intended for insertion in an intervertebral space. However, the Sheppard implant lacks the advantage of maintaining full contact with the vertebrae. U.S. Pat. No. 4,863,477 to Monson discloses a synthetic intervertebral disk prosthesis composed of a rubber-type material having a hollow interior. The interior may be filled with fluid imparting a certain degree of resiliency to the prosthesis. One disadvantage of the Monson prosthesis, however, is that in the anatomical context of the intervertebral space, its design provides very little stability. Thus, the need for a truly stable yet fully flexible artificial intervertebral disk prosthesis and implant exists and is now disclosed.

SUMMARY OF THE INVENTION

A synthetic intervertebral disk prosthesis or implant is described for implementation into the disk space after surgical removal of a diseased or damaged intervertebral disk. Implants according to this invention have a member for adapting the anatomical region of the disk space and apparatus for expanding the member so it conforms to a portion of that space.

In one embodiment the disk is comprised of a silastic sheath in which a plurality of multisized springs are contained. A plurality of sharp engaging or spiked means extend upwardly from the superior portion and downwardly from the inferior portion of the sheath. After implantation, the silastic sheath is filled with a volume of fluid to create resiliency and induce flexibility.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

BRIEF DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

In the accompanying drawings.

DETAILED DESCRIPTION OF THE INVENTION

The disk prosthesis and implants of the present invention can be understood with reference to FIGS. 1 to 4, in which like numerals represent like parts.

Figure 1:
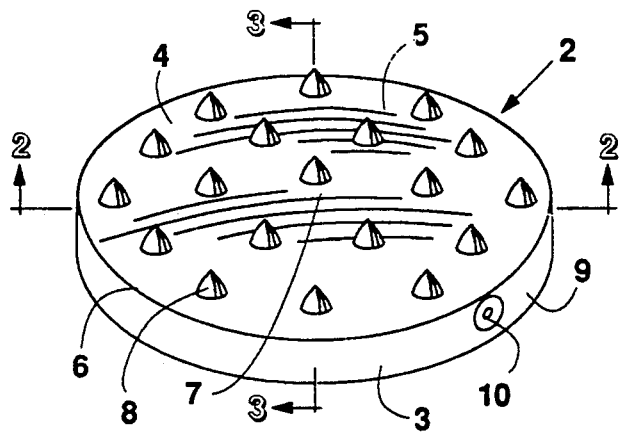
FIG. 1 is a top plan view of a synthetic intervertebral disk prosthesis of the present invention.

FIG. 1 depicts a typical spring loaded, middle expandable total disk prosthesis 2 of the invention. Disk prosthesis 2 is comprised of a strong thin elastic bag 4. Generally, the outer edge 3 of the fully formed disk 2 will be about one centimeter in thickness and a center region 7 of the disk will be about 1.75 centimeters in thickness. The disk prosthesis 2 tapers from center region 7 to the outer region 6 in all directions radially from the center region 7. The interior surface and superior surface of the disk prosthesis 2 are provided with a plurality of spikes 8 extending upwardly from the superior surfaces and downwardly from the inferior surface 9 therefrom for engagement of the vertebra. The disk prosthesis 2 is expandable by injecting a liquid or gas substance through a port 10. Suitable substances for injection include, but are not limited to, saline, mineral oil, air, and oxygen. The disk prosthesis 2 will expand like a balloon to its full dimensions and tightly fit into the disk space.

Figure 2:
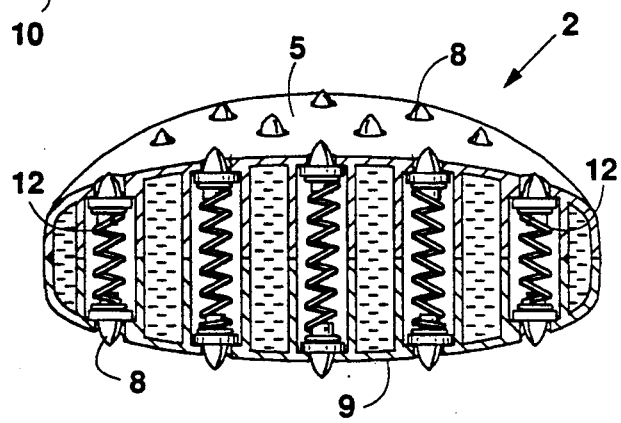
FIG. 2 is a cross sectional view of the device of FIG. 1 in coronal plane.
Figure 3:
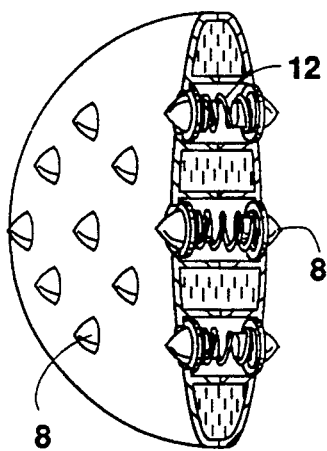
FIG. 3 is cross sectional view of the device of FIG. 1 in the sagittal plane.

FIG. 2, a cross-sectional view of disk prosthesis 2, shows that the disk prosthesis 2 of the present invention contains a plurality of compression springs 12 extending vertically between the superior 5 and inferior 9 surfaces, at various strengths and lengths to yieldably urge the superior 5 and inferior 9 surfaces away from each other.

Figure 4:
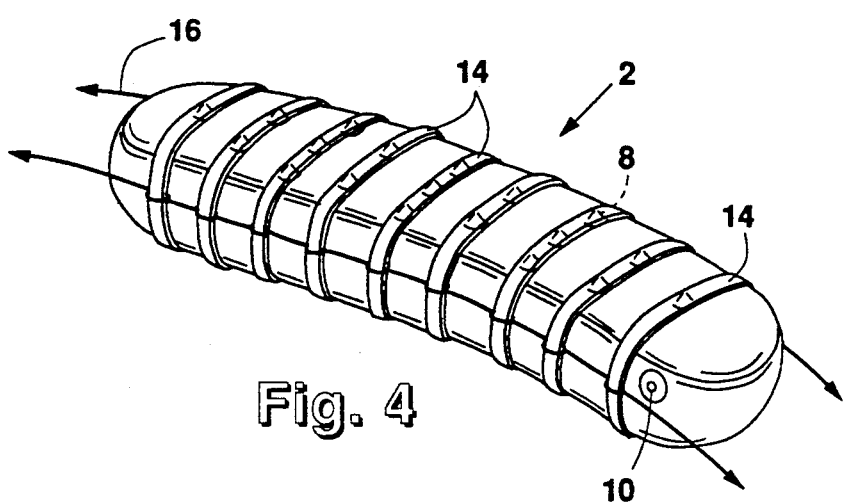
FIG. 4 depicts a side elevational view of the present invention in its pre-expansion form ready for insertion into the disk space.

FIG. 4 depicts a side elevational view of the compressed form of the present invention. When disk prosthesis 2 is empty, it contains only the plurality of springs 12 within an elastic bag 4. This can be rolled up into a tight bundle so that the whole prosthesis 2 has a rectangular shape. Disk prosthesis 2 of FIG. 4 shows injection port 10 used for injection of liquids and/or gases. Suitable liquids and gases include saline, air, and oxygen or any other liquid or gas which causes expansion of the prosthesis. Bands 14 of reinforced silastic encircle disk prosthesis 2 so as to maintain disk prosthesis 2 in a shape and size suitable for insertion through a one square centimeter opening into the disk space. In addition, bands 14 hold down strings 16. Strings 16 are pulled after insertion of disk prosthesis 2 into the disk space thus breaking bands 14 and allowing initial expansion of disk prosthesis 2 caused by the release of springs 12. Subsequently, a suitable liquid and/or gas is injected through port 10 causing complete expansion of disk prosthesis 2 for a very tight fit in the disk space. In addition, the spikes 8 hold disk prosthesis 2 into the vertebral bodies of the spine thus inhibiting or preventing movement of the disk within the intervertebral disk space. As disk prosthesis 2 is expanded in the center region 7 there is no risk of extrusion out into the intervertebral disk space.

The surgical introduction of disk prosthesis 2 can provide increased or maximum stability. Different sizes of the disk prosthesis of the present invention may be provided for insertion into lumbar, thoracic and cervical disks. The artificial disk prosthesis may be composed of any biologically compatible material, e.g. rubber, silicone-rubber compounds, plastic, or plastic-rubber compounds.

The same plug in smaller dimensions can be used in the thoracic and cervical levels where indicated. In the neck this can be used following anterior cervical diskectomy without the risk of the plug migrating anteriorly or posteriorly.

Generally, the height of the substantially oval disk prosthesis of the present invention is from about 1 to about 1.5 cm at the periphery and from about 1.50 to about 2.5 cm in the center region. Generally, the diameter of the disk prosthesis of the present invention is from 4 to about 6 cm from side to side at its longest diameter and from about 3 to about 4 cm from side to side in the perpendicular direction.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to confer the invention broadly in whatever form its principles may be utilized. The present invention is, therefore, well adapted to carry out the objects and obtain the ends and advantages mentioned, as well as others inherent therein.

I claim:

1. An artificial intervertebral disk implant for disposition in the space between two vertebrae after removal of a disk therefrom comprising:

(a) a sheath forming a fluid tight bag having a tapered and substantially oval shape, the tapered surfaces of the oval defining superior and inferior surfaces of the bag, said bag being comprised of a soft, pliable biologically compatible material having a plurality of spiked means formed in the superior and inferior surfaces for stably engaging said implant to the surfaces of the adjacent vertebrae for compressing into a tight bundle for insertion of the implant into the space between two vertebrae, (b) said sheath containing a plurality of multisized spring means positioned between the superior and inferior portions of said sheath and adapted to yieldably urge said surfaces away from each other whereby the shape of the implant after insertion into the space between two vertebrae and expansion conforms to the shape of the space between two vertebrae, and (c) said sheath having a port for receiving injection of fluid therethrough for expanding said bag to form said implant.

2. An artificial intervertebral disk prosthesis of claim 1, wherein said biologically compatible material is selected from a group consisting of rubber, silicone-rubber compounds, plastic, and rubber-plastic compounds.

3. An artificial intervertebral disk prosthesis of claim 1, wherein the fluid injected through said port is a liquid.

4. An artificial intervertebral disk prosthesis of claim 1, wherein said fluid is selected from a group consisting of mineral oil, saline, air and oxygen.

5. An artificial intervertebral disk prosthesis of claim 1, wherein the fluid injected through said port is a gas.

6. An artificial intervertebral disk prosthesis of claim 5, wherein said gas is selected from a group consisting of air and oxygen.

7. A method of implanting an artificial intervertebral disk prosthesis into the space between two vertebrae after removal of a diseased or damaged intervertebral disk, comprising the steps of:

(a) removing air from within a fluid-tight cavity of a disk prosthesis, said disk prosthesis comprising a substantially oval sheath having a fluid-tight interior comprised of a soft, pliable biologically compatible material, said sheath containing a plurality of multisized spring means positioned between a superior and an inferior surface of said sheath and adapted to yieldably urge said surfaces away from each other toward the two vertebrae, said sheath having a port for receiving injection of fluid, (b) compressing said disk prosthesis into a tight bundle;

(c) placing bands around said disk prosthesis so as to maintain said tight bundle, said bands covering pullable strings on each end of said prosthesis;

(d) positioning said prosthesis into the space between the surfaces of the two adjacent vertebrae;

(e) pulling said strings thereby breaking said bands allowing said prosthesis to expand; and (f) injecting a fluid into said cavity to inflate the prosthesis.

8. A method of implanting an artificial intervertebral disk implant of claim 7, wherein the fluid injected is a liquid.

9. A method of implanting an artificial intervertebral disk implant of claim 8, wherein said liquid is selected from a group consisting of saline and mineral oil.

10. A method of implanting an artificial intervertebral disk implant of claim 7, wherein the fluid injected is a gas.

11. A method of implanting an artificial intervertebral disk implant of claim 10, wherein said gas is selected from a group consisting of oxygen and air.

12. A method of implanting an artificial intervertebral disk implant of claim 7 wherein said superior and inferior surfaces of said sheath are provided with spiked means for stably engaging said implant to the surfaces of the adjacent vertebrae.

* * * * *